United States Patent
Dotson et al.

(10) Patent No.: US 10,865,177 B2
(45) Date of Patent: Dec. 15, 2020

(54) PROCESS FOR MAKING HIGH PURITY SALTS

(71) Applicant: Milliken & Company, Spartanburg, SC (US)

(72) Inventors: Darin L. Dotson, Moore, SC (US); Xiaoying Wang, Puyang (CN); Rui Liu, Puyang (CN)

(73) Assignee: Milliken & Company, Spartanburg, SC (US)

(*) Notice: Subject to any disclaimer, the term of this patent is extended or adjusted under 35 U.S.C. 154(b) by 0 days.

(21) Appl. No.: 16/437,698

(22) Filed: Jun. 11, 2019

(65) Prior Publication Data

US 2020/0308091 A1    Oct. 1, 2020

Related U.S. Application Data

(60) Provisional application No. 62/693,085, filed on Jul. 2, 2018.

(51) Int. Cl.
*C07C 51/41* (2006.01)
*C07C 51/42* (2006.01)

(52) U.S. Cl.
CPC ............ *C07C 51/412* (2013.01); *C07C 51/42* (2013.01)

(58) Field of Classification Search
CPC .............................. C07C 51/412; C07C 51/42
USPC .......................................................... 554/156
See application file for complete search history.

(56) References Cited

U.S. PATENT DOCUMENTS

| 2003/0027908 | A1  | 2/2003  | Dotson et al. |
| 2004/0220311 | A1* | 11/2004 | Dotson ................ C08K 5/098 |
|              |     |         | 524/394 |
| 2004/0220331 | A1  | 11/2004 | Dotson et al. |

OTHER PUBLICATIONS

PCT/US2019/036533 International Search Report—filed Jun. 11, 2019, 5 pages.
PCT/US2019/036533 Written Opinion of the International Searching Authority, filed Jun. 11, 2019, 6 pages.

* cited by examiner

*Primary Examiner* — Deborah D Carr
(74) *Attorney, Agent, or Firm* — Robert M. Lanning

(57) ABSTRACT

A process for making a high purity salt comprises the steps of providing an organic compound, providing a metal salt, adding the metal salt and organic compound to an aqueous medium, heating the reaction mixture to react the organic compound and the metal salt to form an organic salt, collecting the organic salt, exposing the collected organic salt to microwave radiation, and exposing the collected organic salt to infrared radiation.

10 Claims, No Drawings

PROCESS FOR MAKING HIGH PURITY SALTS

CROSS-REFERENCE TO RELATED APPLICATIONS

This application claims, pursuant to 35 U.S.C. § 119(e), priority to and the benefit of the filing date of U.S. Patent Application No. 62/693,085, which was filed on Jul. 2, 2018, the contents of which are hereby incorporated by reference.

TECHNICAL FIELD OF THE INVENTION

This patent application relates to a process for making high purity salts. In particular, the patent application describes a method for making salts of cis-cyclohexane-1, 2-dicarboxylic acid with low levels of trans-cyclohexane-1, 2-dicarboxylate salts.

BACKGROUND

Salts produced in aqueous media typically are dried to a relatively low moisture content prior to further use. The processes used to dry such salts typically are optimized to maximize throughput. In other words, the drying conditions are selected to dry the maximum amount of salt in a minimum amount of time. Such rapid drying of the salt can have unintended consequences. For instance, high heat can lead to degradation of some of the salt, decreasing the overall purity of the final product. Also, excessive heat can cause rearrangement reactions in certain salts, especially in salts of organic acids (organic salts). These rearrangement reactions will affect the isomeric purity (e.g., stereoisomeric purity) of the resulting salt. And changes in the isomeric purity of the salt can render it unsuitable for certain uses, such as pharmaceutical or food contact uses.

A need therefore remains for a process for producing salts (e.g., salts of organic acids) that achieves acceptable throughput while maintaining the isomeric purity (e.g., stereoisomeric purity) of the final product. The process described herein is believed to meet such need.

BRIEF SUMMARY OF THE INVENTION

In a first embodiment, the invention provides a process for making a high purity salt, the process comprising the steps of:

(a) providing an organic compound selected from the group consisting of cis-cyclohexane-1,2-dicarboxylic acid anhydride, cis-cyclohexane-1,2-dicarboxylic acid, and mixtures thereof;

(b) providing a metal salt selected from the group consisting of metal hydroxides and metal carbonates, the metal salt comprising a metal selected from the group consisting of alkali metals and alkaline earth metals;

(c) adding the metal salt and the organic compound to an aqueous medium to produce a reaction mixture;

(d) heating the reaction mixture to a temperature of about 65° C. to about 80° C. to react the organic compound and the metal salt and form an organic salt;

(e) collecting the organic salt from the aqueous medium;

(f) exposing the collected organic salt to microwave radiation having a frequency of about 900 MHz to about 2,500 MHz to reduce the moisture content of the organic salt to about 20% or less; and (g) exposing the organic salt from step (f) to infrared radiation having a frequency of about $9.9 \times 10^4$ GHz to about $3 \times 10^5$ GHz to reduce the moisture content of the organic salt to about 7% or less.

DETAILED DESCRIPTION OF THE INVENTION

In a first embodiment, the invention provides a process for making a high purity salt. The process generally comprises the steps of providing an organic compound (e.g., an organic acid or an anhydride thereof), providing a metal salt, adding the metal salt and organic compound to an aqueous medium, reacting the organic compound and metal salt to form an organic salt, collecting the organic salt from the aqueous medium, exposing the collected organic salt to microwave radiation, and exposing the organic salt to infrared radiation. The process is believed to yield an organic salt having an acceptably low moisture content and high purity (e.g., isomeric purity).

The process can utilize any suitable organic compound. Preferably, the organic compound is an organic acid, more preferably a carboxylic acid or an anhydride thereof. In one preferred embodiment, the organic compound is selected from the group consisting of cyclohexane-1,2-dicarboxylic acid anhydride, cyclohexane-1,2-dicarboxylic acid, and mixtures thereof. In a particularly preferred embodiment, the organic compound is selected from the group consisting of cis-cyclohexane-1,2-dicarboxylic acid anhydride, cis-cyclohexane-1,2-dicarboxylic acid, and mixtures thereof. In another preferred embodiment, the organic compound is selected from the group consisting of cis-cyclohexane-1,2-dicarboxylic acid anhydride. When the organic compound is selected from the group consisting of cis-cyclohexane-1,2-dicarboxylic acid anhydride, cis-cyclohexane-1,2-dicarboxylic acid, and mixtures thereof, the organic compound preferably contains relatively little of the corresponding trans isomers. Thus, in a preferred embodiment, the organic compound contains about 1.5 mol. % or less (e.g., about 1 mol. % or less) trans-cyclohexane-1,2-dicarboxylic acid anhydride or trans-cyclohexane-1,2-dicarboxylic acid.

The process can utilize any suitable metal salt. Preferably, the metal salt is selected from the group consisting of metal hydroxides and metal carbonates. Preferably, the metal salt comprises a metal selected from the group consisting of alkali metals and alkaline earth metals. In another preferred embodiment, the metal salt comprises a metal selected from the group consisting of alkaline earth metals. Suitable metal salts compounds include, but are not limited to, calcium hydroxide, sodium hydroxide, calcium carbonate, sodium carbonate, and mixtures thereof. In a preferred embodiment, the metal salt is selected from the group consisting of calcium hydroxide and calcium carbonate. In another preferred embodiment, the metal salt is calcium hydroxide. In yet another preferred embodiment, the metal salt is calcium carbonate.

In one step, the process entails the addition of the metal salt and the organic compound to an aqueous medium to produce a reaction mixture. The two compounds can be added to the aqueous medium or in any suitable order. In certain preferred embodiments (e.g., when a relatively insoluble metal salt is employed), the organic compound preferably is first added to the aqueous medium, and the resulting mixture is stirred or otherwise agitated until the organic compound has completely dissolved in the aqueous medium. In such an embodiment, the metal salt is then added, and the resulting mixture preferably is stirred or otherwise agitated to produce a substantially homogeneous reaction mixture. For example, when an insoluble metal salt is used, the mixture preferably is stirred or otherwise agitated to disperse the metal hydroxide compound in the reaction mixture.

The organic compound and the metal salt can be added to the aqueous medium in any suitable amounts. Preferably, to optimize purity of the resulting organic salt, the organic compound and the metal salt are added to the aqueous medium in stoichiometric amounts. However, when a soluble metal salt (e.g., sodium hydroxide) is employed, the metal salt can be added in a slight stoichiometric excess. In such cases, the excess soluble metal hydroxide compound will remain dissolved in the aqueous medium and can be easily separated from the target organic salt.

The reaction mixture preferably is heated to drive the reaction between the organic compound and the metal salt that forms the desired organic salt. The reaction mixture can be heated to any suitable temperature. In a preferred embodiment, the reaction mixture is heated to a temperature of about 30° C. or more, about 40° C. or more, about 50° C. or more, about 60° C. or more, about 80° C. or more, about 90° C. or more, about 100° C. or more, or the boiling point of the reaction mixture. In a preferred embodiment, the reaction mixtures is heated to a temperature of about 65° C. to about 80° C. The reaction mixture can be heated to the desired temperature for any suitable amount of time. Preferably, the reaction mixture is heated to the desired temperature until the reaction between the organic compound and the metal salt is complete.

In some embodiments of the process, the product produced by the reaction between the metal salt and the organic compound is the desired organic salt. In such embodiments, the organic salt can be collected from the aqueous medium as described below. In other embodiments of the process, the product produced by the reaction between the metal salt and the organic compound can be further reacted or treated to produce the desired organic salt. For example, when the product produced by the reaction between the metal salt and the organic compound is a water-soluble organic salt, this water-soluble organic salt can be further reacted with a second salt in an ion exchange reaction to produce the desired organic salt. Suitable second salts for such ion exchange reactions include, but are not limited to, calcium salts, lithium salts, strontium salts, aluminum salts, and mixtures thereof.

Following the reaction steps, the target organic salt is collected from the aqueous medium. The target organic salt can be collected or separated from the aqueous medium using any suitable method. For example, the aqueous medium can be filtered to separate the target organic salt. Alternatively, the target organic salt can be removed from the aqueous medium using a centrifuge.

Following separation and collection, the collected organic salt can be conveyed directly to the drying process, as described below. Alternatively, the collected organic salt can be granulated or milled to provide material having a more uniform particle size. While this step is not necessary for the described process, the efficiency of the drying step is improved when a more uniform particle size material is dried. Preferably, the collected organic salt is granulated to a particle size of about 1 mm or less, about 0.5 mm or less, about 0.4 mm or less, about 0.3 mm or less, or about 0.2 mm or less.

In a first drying step, the collected organic salt is exposed to microwave radiation. The primary purpose of this step is to reduce the free moisture of the collected organic salt to an acceptable level for further drying. The collected organic salt can be exposed to microwave radiation having any suitable frequency. Typically, the frequency of the microwave radiation is from about 900 MHz to about 2,500 MHz. More specifically, the frequency of the microwave radiation preferably is about 915 MHz or about 2,450 MHz, or a combination of 915 MHz and 2,450 MHz microwave radiation can be used. The microwave radiation can be of any suitable intensity. The intensity used will depend upon several factors, such as the initial moisture content of the collected organic salt, the desired final moisture content of the collected organic salt, and the desired throughput of the microwave drying step. Preferably, the energy flux of the microwave radiation is about $2 \times 10^7$ $J \cdot m^{-2} \cdot s^{-1}$ or more, about $2.1 \times 10^7$ $J \cdot m^{-2} \cdot s^{-1}$ or more, or about $2.15 \times 10^7$ $J \cdot m^{-2} \cdot s^{-1}$ or more (e.g., about $2.16 \times 10^7$ $J \cdot m^{-2} \cdot s^{-1}$ or more). The energy flux of the microwave radiation preferably is about $1 \times 10^8$ $J \cdot m^{-2} \cdot s^{-1}$ or less, about $9 \times 10^7$ $J \cdot m^{-2} \cdot s^{-1}$ or less, about $8 \times 10^7$ $J \cdot m^{-2} \cdot s^{-1}$ or less, about $7 \times 10^7$ $J \cdot m^{-2} \cdot s^{-1}$ or less, about $6 \times 10^7$ $J \cdot m^{-2} \cdot s^{-1}$ or less, about $5 \times 10^7$ $J \cdot m^{-2} \cdot s^{-1}$ or less, about $4.5 \times 10^7$ $J \cdot m^{-2} \cdot s^{-1}$ or less, about $4.4 \times 10^7$ $J \cdot m^{-2} \cdot s^{-1}$ or less, or about $4.35 \times 10^7$ $J \cdot m^{-2} \cdot s^{-1}$ or less (e.g., about $4.32 \times 10^7$ $J \cdot m^{-2} \cdot s^{-1}$ or less). Preferably, the energy flux of the microwave radiation is about $2 \times 10^7$ $J \cdot m^{-2} \cdot s^{-1}$ to about $4.5 \times 10^7$ $J \cdot m^{-2} \cdot s^{-1}$, about $2.1 \times 10^7$ $J \cdot m^{-2} \cdot s^{-1}$ to about $4.4 \times 10^7$ $J \cdot m^{-2} \cdot s^{-1}$, about $2.15 \times 10^7$ $J \cdot m^{-2} \cdot s^{-1}$ to about $4.35 \times 10^7$ $J \cdot m^{-2} \cdot s^{-1}$, or about $2.16 \times 10^7$ $J \cdot m^{-2} \cdot s^{-1}$ to about $4.32 \times 10^7$ $J \cdot m^{-2} \cdot s^{-1}$.

The collected organic salt can be exposed to the microwave radiation for any suitable time. Preferably, the collected organic salt is exposed to the microwave radiation for a sufficient time to reduce the moisture content of the organic salt to about 20% or less. At the preferred energy flux described above, the collected organic salt is exposed to the microwave radiation for about 30 minutes or more, or about 40 minutes or more. The collected organic salt preferably is exposed to the microwave radiation for about 60 minutes or less or about 50 minutes of less. Thus, at the preferred energy flux described above, the collected organic salt preferably is exposed to the microwave radiation for about 30 minutes to about 60 minutes, or about 40 minutes to about 50 minutes.

Prior to exposure to the microwave radiation, the collected organic salt can be deposited onto a conveyor which passes under the microwave emitter(s). In depositing the material on the conveyor, the collected organic salt preferably is deposited in a substantially uniform layer. This helps to ensure even drying of the collected organic salt. Further, the thickness of the deposited organic salt preferably is no greater than 3 cm, more preferably no greater than 2 cm.

In a second drying step, the collected organic salt is exposed to infrared radiation. The purpose of this step is to further reduce the free moisture of the collected organic salt and, if desired, also to at least partially remove any waters of hydration that may be present in the collected organic salt. The collected organic salt can be exposed to infrared radiation having any suitable frequency. Typically, the frequency of the microwave radiation is from about $9.9 \times 10^4$ GHz to about $3 \times 10^5$ GHz. The infrared radiation can be of any suitable intensity. The intensity used will depend upon several factors, such as the moisture content of the collected organic salt at the start of this drying step, the desired final moisture content of the collected organic salt, and the desired throughput of the infrared drying step. Preferably, the energy flux of the infrared radiation is about 1,900 $J \cdot m^{-2} \cdot s^{-1}$ or more, about 2,000 $J \cdot m^{-2} \cdot s^{-1}$ or more, or about 2,100 $J \cdot m^{-2} \cdot s^{-1}$ or more. The energy flux of the infrared radiation preferably is about 10,000 $J \cdot m^{-2} \cdot s^{-1}$ or less, about 9,000 J·m$^{-2}$·s$^{-1}$ or less, about 8,000 J·m$^{-2}$·s$^{-1}$ or less, about 7,000 J·m$^{-2}$·s$^{-1}$ or less, about 6,000 J·m$^{-2}$·s$^{-1}$ or less, about 5,000 J·m$^{-2}$·s$^{-1}$ or less, about 4,000 J·m$^{-2}$·s$^{-1}$ or less, about 3,000 J·m$^{-2}$·s$^{-1}$ or less, about 2,500 J·m$^{-2}$·s$^{-1}$ or less, about 2,300 J·m$^{-2}$·s$^{-1}$ or less, or about 2,250 J·m$^{-2}$·s$^{-1}$ or less (e.g., about 2,210 J·m$^{-2}$·s$^{-1}$ or less). Preferably, the energy flux of the infrared radiation is about 1,900 J·m$^{-2}$·s$^{-1}$ to about 2,500 J·m$^{-2}$·s$^{-1}$, about 2,000 J·m$^{-2}$·s$^{-1}$ to about 2,300 J·m$^{-2}$·s$^{-1}$, about 2,100 J·m$^{-2}$·s$^{-1}$ to about 2,250 J·m$^{-2}$·s$^{-1}$, or about 2,100 J·m$^{-2}$·s$^{-1}$ to about 2,210 J·m$^{-2}$·s$^{-1}$.

The collected organic salt can be exposed to the infrared radiation for any suitable time. Preferably, the collected organic salt is exposed to the infrared radiation for a sufficient time to reduce the moisture content of the organic salt to about 7% or less, about 6% or less, about 5% or less, about 4% or less, about 3% or less, about 2% or less, or about 1.5% or less. At the preferred energy flux described above, the collected organic salt is exposed to the infrared radiation for about 60 minutes or more, about 75 minutes or more, or about 90 minutes or more. The collected organic salt preferably is exposed to the infrared radiation for about 180 minutes or less, about 150 minutes of less, or about 120 minutes or less. Thus, at the preferred energy flux described above, the collected organic salt preferably is exposed to the infrared radiation for about 60 minutes to about 180 minutes, about 75 minutes to about 150 minutes, or about 90 minutes to about 120 minutes.

In a preferred embodiment of the process, the organic salt produced by the claimed process is a cis-cyclohexane-1,2-dicarboxylate salt. In a particularly preferred embodiment, the organic salt is calcium cis-cyclohexane-1,2-dicarboxylate. As noted above, the process described herein is believed to be well-suited to the production of organic salts with relatively high isomeric purity (e.g., stereoisomeric purity). Thus, when the organic salt is a cis-cyclohexane-1,2-dicarboxylate salt, the organic salt preferably contains about 2.5 mol. % or less, about 1.5 mol. % or less, or about 1 mol. % or less, of trans-cyclohexane-1,2-dicarboxylate salts.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A process for making a high purity salt, the process comprising the steps of:
    (a) providing an organic compound selected from the group consisting of cis-cyclohexane-1,2-dicarboxylic acid anhydride, cis-cyclohexane-1,2-dicarboxylic acid, and mixtures thereof;
    (b) providing a metal salt selected from the group consisting of metal hydroxides and metal carbonates, the metal salt comprising a metal selected from the group consisting of alkali metals and alkaline earth metals;
    (c) adding the metal salt and the organic compound to an aqueous medium to produce a reaction mixture;
    (d) heating the reaction mixture to a temperature of about 65° C. to about 80° C. to react the organic compound and the metal salt and form an organic salt;
    (e) collecting the organic salt from the aqueous medium;
    (f) exposing the collected organic salt to microwave radiation having a frequency of about 900 MHz to about 2,500 MHz to reduce the moisture content of the organic salt to about 20% or less; and
    (g) exposing the organic salt from step (f) to infrared radiation having a frequency of about $9.9 \times 10^4$ GHz to about $3 \times 10^5$ GHz to reduce the moisture content of the organic salt to about 7% or less.

2. The process of claim 1, wherein the organic compound is cis-cyclohexane-1,2-dicarboxylic acid anhydride.

3. The process of claim 1, wherein the organic compound contains about 1.5 mol. % or less trans-cyclohexane-1,2-dicarboxylic acid anhydride or trans-cyclohexane-1,2-dicarboxylic acid.

4. The process of claim 1, wherein the metal salt is calcium hydroxide.

5. The process of claim 1, wherein the organic salt is calcium cis-cyclohexane-1,2-dicarboxylate.

6. The process of claim 5, wherein the organic salt contains about 2.5 mol. % or less of trans-cyclohexane-1,2-dicarboxylate salts.

7. The process of claim 6, wherein the organic salt contains about 1 mol. % or less of trans-cyclohexane-1,2-dicarboxylate salts.

8. The process of claim 1, wherein the collected organic salt is granulated prior to exposure to the microwave radiation.

9. The process of claim 1, wherein the energy flux of the microwave radiation is about $2 \times 10^7$ J·m$^{-2}$·s$^{-1}$ to about $4.5 \times 10^7$ J·m$^{-2}$·s$^{-1}$.

10. The process of claim 1, wherein the energy flux of the infrared radiation is about 1,900 $J \cdot m^{-2} \cdot s^{-1}$ to about 2,500 $J \cdot m^{-2} \cdot s^{-1}$.

\* \* \* \* \*